(12) United States Patent
Ho et al.

(10) Patent No.: US 7,598,375 B2
(45) Date of Patent: Oct. 6, 2009

(54) METHOD OF ACYLATING MAYTANSINOL WITH CHIRAL AMINO ACIDS

(75) Inventors: Guojie Ho, Sudbury, MA (US); Darren J. Carrozzella, Cambridge, MA (US)

(73) Assignee: Millenium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 11/500,378

(22) Filed: Aug. 8, 2006

(65) Prior Publication Data

US 2007/0037972 A1  Feb. 15, 2007

Related U.S. Application Data

(60) Provisional application No. 60/706,694, filed on Aug. 9, 2005.

(51) Int. Cl.
*C07D 491/04* (2006.01)

(52) U.S. Cl. ..................................................... 540/456

(58) Field of Classification Search .................. 540/456
See application file for complete search history.

(56) References Cited

U.S. PATENT DOCUMENTS

| 4,260,609 A | 4/1981 | Baldwin et al. |
| 6,333,410 B1 | 12/2001 | Chari et al. |
| 7,301,019 B2 * | 11/2007 | Widdison et al. ........... 540/456 |

FOREIGN PATENT DOCUMENTS

| WO | WO 03/074551 A2 | 12/2003 |
| WO | WO 2006/078809 A2 | 7/2006 |

\* cited by examiner

*Primary Examiner*—Bruck Kifle
(74) *Attorney, Agent, or Firm*—Sughrue Mion, PLLC

(57) ABSTRACT

This invention provides a method for making maytansinoids having a chiral amino acid side chain, such as DM1 and DM4 that are used to treat cancer. According to this method, the side chain may be added with little epimerization of the amino acid chiral center.

10 Claims, No Drawings

METHOD OF ACYLATING MAYTANSINOL WITH CHIRAL AMINO ACIDS

This application claims priority from U.S. Provisional Application No. 60/706,694 filed Aug. 9, 2005.

FIELD OF THE INVENTION

The present invention relates to a method for making maytansinoids with chiral amino acid side chains. The maytansinoids may be conjugated to cell-binding agents such as antibodies and are useful therapeutics, especially for the treatment of cancer.

BACKGROUND OF THE INVENTION

Maytansinoids are potent anti-cancer compounds, the use of which is limited by their toxicity. One approach for managing the toxicity of these agents is to link the maytansinoid to an antibody that specifically targets the tumor. Antibody-maytansinoid conjugates have been shown to have potent anti-tumor activity in human xenograft studies (C. Liu et al., Proc. Natl. Acad. Sci. USA 93, 8618-8623 (1996)). MLN2704 is such a conjugate and is currently in Phase II clinical trials for the treatment of metastatic androgen independent prostate cancer. MLN2704 consists of a targeting monoclonal antibody vehicle (T-MAV) designed to deliver a lethal payload specifically to tumor cells that express on their surfaces prostate-specific membrane antigen (PSMA). In the case of MLN2704, the lethal payload consists of the chemotherapeutic maytansinoid DM1, which has been conjugated to the T-MAV. In preclinical studies, after binding to PSMA on the surface of a tumor cell, the T-MAV was transported inside the cell and the tumor cell was destroyed by the DM1. PSMA is expressed on almost all prostate cancer cells, both primary and metastatic, and its abundance on the cell surface increases as the cancer progresses. These findings suggest that MLN2704 has potential as a specific new therapy for prostate cancer. (See www.mlnm.com/rd/oncology/candidates/mln2704.asp).

DM1 has been prepared from maytansinol:

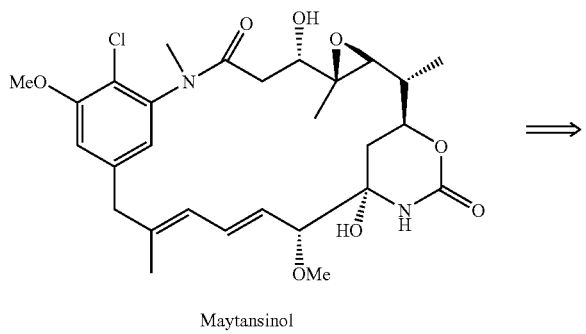

Maytansinol

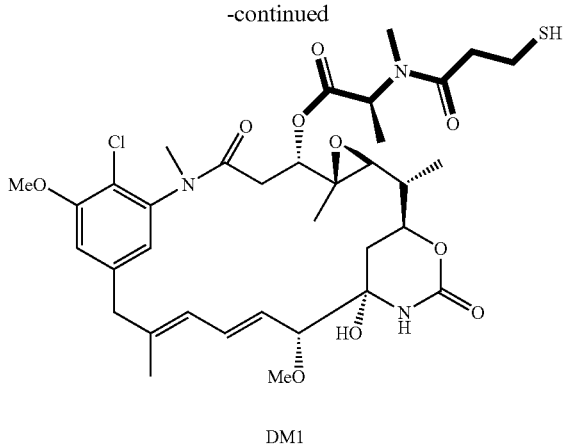

DM1

In the structure of DM1 shown above the chiral side chain in bold type may be attached to a linker group that connects the toxic maytansinoid and an antibody that is used to target the tumor. A two-step conversion of maytansinol to DM1 is known in the art (see U.S. Pat. No. 5,208,020). The first step is the coupling of maytansinol with N-methyl-N-(3-methyldithiopropanoyl)-L-alanine: $HO_2CCH(CH_3)N(CH_3)COCH_2CH_2SSMe$, the preparation of which is described in U.S. Pat. No. 6,570,024. In the second step, the —SSMe group is reduced to the —SH group of DM1. A disadvantage of this synthesis is the epimerization of the side chain chiral center that occurs in the first step. Even under relatively mild coupling conditions (DCC and $ZnCl_2$), complete epimerization occurs. Not only does the epimerization cause low yield of desired product, but the unwanted diastereomer must be removed by tedious chromatographic separation.

EP Patent Application Publication No. 0021173 describes the synthesis of maytansinol 3-(S)- and 3-(R)-α-N-methylaminopropionate from the corresponding maytansinol 3-α-(N-methyl-N-tert-butoxycarbonyl)aminopropionate. The latter compound was prepared by coupling maytansinol with N-tert-butoxycarbonyl-N-methyl-L-alanine in the presence of DCC. This coupling reaction provided low yields of both the 3-(S)- and 3-(R)-epimers.

Providing DM1 and other maytansinoids with chiral side chain linkers is costly. Starting maytansinol is expensive and the coupling reaction typically results in a low yield, largely because of epimerization when the side chain is attached in the coupling reaction. Accordingly, there is a need for higher yielding methods that avoid or reduce epimerization in the coupling of the side chain linker.

DESCRIPTION OF THE INVENTION

This invention relates to a method of making maytansinoids, such as DM1 or DM4. The key step in the method is the coupling of maytansinol or an analogue thereof with a chiral 4-alkyl-1,3-oxazolidine-2,5-dione or 3,4-dialkyl-1,3-oxazolidine-2,5-dione. These 1,3-oxazolidine-2,5-diones are N-carboxyanhydride derivatives of α-amino acids (NCAs). It now has been found that NCAs, which may be obtained from enantiomerically pure naturally-occurring amino acids, are especially useful coupling partners because the configuration of the amino acid chiral center is highly preserved in the coupling reaction. The present invention is exemplified using (S)-3,4-dimethyl-1,3-oxazolidine-2,5-dione (1, N-methylalanine-N-carboxyanhydride or N-MeAla NCA), which is particularly useful for the preparation of DM1 and DM4. The coupling step with 1 provides, with high diastereomeric purity, a maytansinol ester intermediate having an N-methyl-alanine side chain. The intermediate obtained from the NCA coupling reaction is useful for making a variety of maytansinoids with chiral amino acid side chains. The side chains may be attached to a linker group for conjugation of the maytansinoid to various antibodies for the treatment of cancer.

Scheme 1

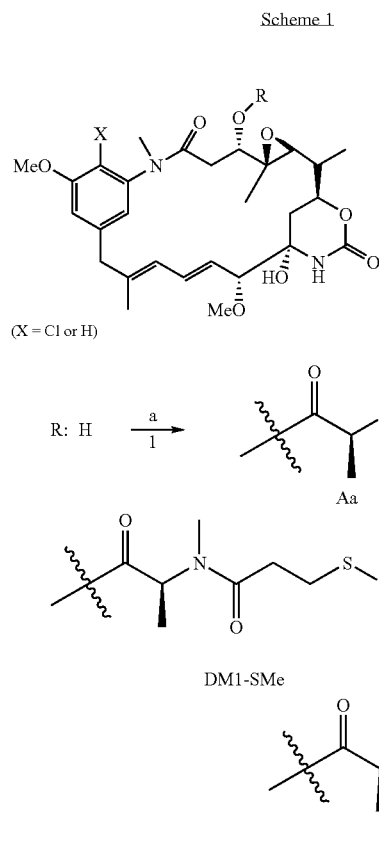

(X = Cl or H)

Scheme 1 above illustrates the method as part of an overall route for the preparation of DM1 (X=Cl) with high diastereomeric purity. The method comprises the step of preparing maytansinol 3-(S)-α-N-methylaminopropionate (A) by treating maytansinol (R=H) with homochiral or enantiomerically-enriched 3,4-dimethyl-1,3-oxazolidine-2,5-dione (1). This step is sometimes referred to herein as the coupling reaction with 1 (or N-MeAla NCA). The use of 1 in this manner is advantageous over the prior art by avoiding complete or near complete epimerization of the N-methyl-alanine side chain. The reaction proceeds with only a small degree of epimerization, providing mostly desired maytansinol 3-(S)-α-N-methylaminopropionate (or 3-(S)-Aa, L-isomer) as opposed to undesired maytansinol 3-(R)-α-N-methylaminopropionate (or 3-(R)-Aa, D-isomer). Under certain conditions described below, one may obtain compound Aa having a ratio of 3-(S)-Aa to 3-(R)-Aa as high as about 98:2 to 99:1.

The method outlined in Scheme 1 may be extended generally to other NCAs by replacing 1 with a compound of formula 2:

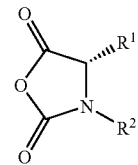

where $R^1$ is an amino acid side chain and $R^2$ is hydrogen, $C_{1-6}$ alkyl, aryl or aralkyl. Preferably $R^1$ is an amino acid side chain of a naturally-occurring α-amino acid, and more preferably $R^1$ is a $C_{1-6}$ alkyl. Preferably, $R^2$ is hydrogen or a $C_{1-6}$ alkyl. Accordingly, one embodiment of the invention relates to a method of making a compound of formula A:

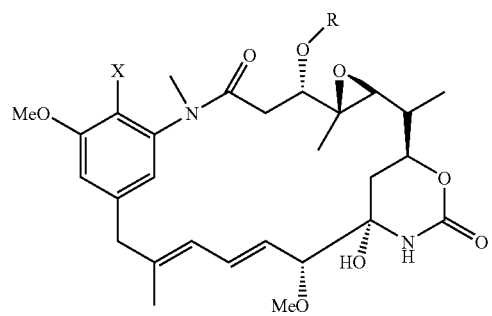

where:
X is Cl or H, and
R is

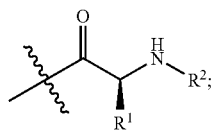

$R^1$ is an amino acid side chain;
$R^2$ is hydrogen, a $C_{1-6}$ alkyl, aryl or aralkyl;
said method comprising:
(a) providing a mixture comprising:
  (i) a starting material which has a formula identical to formula A except that R is hydrogen,
  (ii) a compound of formula 2:

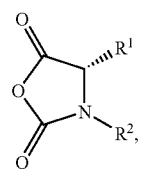

(iii) a Lewis acid,
  (iv) a non-nucleophilic base and
  (v) an organic solvent;
(b) allowing the mixture of step (a) to react until some, usually at least 20%, of the starting material is converted to the compound of formula A;

(c) removing crude compound of formula A from the mixture of step (b); and
(d) optionally purifying the compound of formula A obtained in step (c).

The $R^1$ amino acid side chain can be those found in naturally-occurring amino acids. Particular examples include small alkyl side chains (1-6 carbons), such as those of alanine, leucine or valine where $R^1$ is methyl, isobutyl or isopropyl, respectively. The $R^2$ aryl group is typically a 5 or 6-membered aromatic ring such as phenyl. Examples of $R^2$ aralkyl groups include aryl groups with a $C_{1-3}$ alkyl chain, such as benzyl or phenethyl. Preferably, $R^2$ is hydrogen or a $C_{1-6}$ alkyl such as methyl.

The general preparation of an N-carboxyanhydride of an amino acid 2, including the preparation of L-3,4-dimethyl-1,3-oxazolidine-2,5-dione (1) from alanine, is described in Tetrahedron, Vol. 50, No. 30, pp. 9051-9060 (1994). The reaction of an NCA, such as 1, with maytansinol is performed in an organic solvent in the presence of a Lewis acid and a hindered, organic base. Unless otherwise indicated, the term "organic solvent" is not limited to a single solvent, but also includes mixtures of organic solvents. For example, the mixture of THF and DMF is encompassed by the term "an organic solvent." Examples of particular organic solvents that may be used include ether solvents such as tetrahydrofuran (THF), 1,2-dimethoxyethane (DME), chlorohydrocarbon solvents such as dichloromethane (DCM), ester solvents such as ethyl acetate and isopropyl acetate, aromatic solvents such as toluene and polar solvents such as dimethylformamide (DMF) and acetonitrile. The amount of solvent is typically in the range of about 5-50 ml of solvent per gram of maytansinol, preferably about 5-20 ml per gram and more preferably about 12-17 ml per gram.

The amount of NCA used in the reaction is typically in the range of about 2-10 equivalents per equivalent of maytansinol. Preferably about 5-7 equivalents of NCA are used in the reaction.

In the coupling reaction of maytansinol with an NCA, the base is a non-nucleophilic base. Suitable for this purpose are hindered organic bases such as a hindered, tertiary amine. Examples of suitable bases include trialkylamines such as diisopropylethylamine. The amount of base is typically in the range of 2-10 equivalents of base per equivalent of maytansinol and preferably about 4-6 equivalents.

The Lewis acid used in the coupling reaction with an NCA is a weak to moderate Lewis acid. Examples of such Lewis acids include zinc triflate —Zn(OTf)$_2$, zinc chloride —ZnCl$_2$, magnesium bromide, magnesium triflate —Mg(OTf)$_2$, copper triflate —Cu(OTf)$_2$, copper(II)bromide —CuBr$_2$ and copper(II)chloride —CuCl$_2$. The amount of Lewis acid is typically in the range of 1.5 to 10 equivalents of Lewis acid per equivalent of maytansinol, preferably about 2 to 4 equivalents.

The reaction temperature of the coupling reaction with the NCA is usually in the range of 0° C. to about 60° C., depending greatly on the choice of solvent and reagents. When DMF is used as a solvent or co-solvent, the temperature is typically in the range of about 15° C. to about 30° C. and more preferably in the range of 15-25° C. As the temperature rises above about 60° C. decomposition of the product may occur. The low end of the temperature range is desirable for obtaining high diastereoselectivity in the product mixture, provided that the temperature is sufficient to get good conversion of starting material to product.

The amount of desired 3-(S)-A diastereomer obtained relative to 3-(R)-A will depend on the reagents and reaction conditions employed. The percent diastereomeric excess (% de) of 3-(S)-A over 3-(R)-A may range from greater than about 40% to as high as about 98-99%. Typically the % de is greater than about 80% and as high as 98-99%. In dichloromethane in the presence of zinc triflate and diisopropylethylamine, the % de for the coupling reaction ranged from about 76% to 95%. Under similar conditions in THF the % de was better than 95%. In an organic solvent mixture consisting of DMF and THF in a 2:1 ratio at about 20° C. and in the presence of zinc triflate, one may obtain 80-90% conversion of starting material to product with a % de greater than 90%. In the coupling reaction with the NCA, it is not necessary that all of the starting maytansinol be consumed. After work-up of the reaction, the crude reaction material containing some starting maytansinol is often suitable for use in the next step without purification. That means that starting maytansinol may be carried through at least another step before it is removed. This crude material used in the next step may contain about 1-80% maytansinol and about 20-99% of the α-amino acid ester of maytansinol, where the % de is in the range of about 40-99%. Typically, the amount of the α-amino acid ester of maytansinol in the crude material is at least 60% and usually at least 70%, where the % de is in the range of 80-99%.

The reaction can be monitored using any standard high pressure liquid chromatography (HPLC) system. As an example, for the present invention the applicants used an Agilent 1100 system equipped with an Agilent ZorBax-CN column (4.6×250 mm). The following conditions were employed to follow the course of the reaction: the injection temperature was 50° C., the injection volume was 5 microliters, the flow rate was 1.0 ml/minute, detection was at 254 nm, and the eluting solvent consisted of 10 mM ammonium acetate (solvent A) and 95:5 acetonitrile:water (solvent B). Gradient elution proceeded from a starting mixture of solvent A:solvent B equal to 55:45 to an A:B solvent mixture of 45:55 over 15 minutes. Under these conditions, the retention time for starting maytansinol is 5.4 minutes and for product 3-(S)-A is 7.3 minutes.

In one example of the present method the following procedure was employed to prepare maytansinol 3-(S)-α-N-methylaminopropionate (Aa). N,N-Diisopropylethylamine (0.21 ml, 1.2 mmol) and L-3,4-dimethyl-oxazolidine-2,5-dione (129 mg, 1.0 mmol) were added to a solution of maytansinol (113 mg, 0.20 mmol) in dry THF (1.7 ml). The mixture was stirred for 2-3 minutes after which time zinc triflate (218 mg, 0.60 mmol) was added. The reaction was stirred at 50-55° C. with occasional monitoring by HPLC. After 26 hours, HPLC analysis indicated that the reaction mixture contained 57.5% of the desired 3-(S)-Aa, 2% of 3-(R)-Aa and 31% of starting maytansinol. After 28 hours the heating was removed and the reaction was allowed to stand at ambient temperature overnight. HPLC analysis showed no change in the reaction profile compared to that taken at 28 hours. Ethyl acetate (3 ml) and saturated sodium bicarbonate solution (2 ml) were added to the reaction mixture. The resulting mixture was stirred for 2-3 minutes, and when stirring stopped the layers separated. The aqueous layer was extracted with fresh ethyl acetate (1.5 ml). The organic layers were combined, washed first with water (2 ml) and then saturated brine solution (1 ml), and dried over sodium sulfate. The solvent was removed under reduced pressure to yield a brown oil and foamy solid. The resulting crude maytansinol 3-(S)-a-N-methylaminopropionate (Aa) may be purified, for example using HPLC, or used directly in the next step.

In a second example of the present method, the following procedure was employed to prepare maytansinol 3-(S)-α-N-methylaminopropionate (Aa). To a solution of maytansinol (120 mg, 0.212 mmol, 1.0 equiv.) in dry THF (1.2 mL) and dry DMF (0.60 mL) was added diisopropylethylamine (222 uL, 6.0 equiv.), Zn(OTf)$_2$ (231 mg, 3.0 equiv.) and NMeAla NCA (138 mg, 5.0 equiv.). The resulting near solution was stirred at ambient temperature and periodically monitored for reaction conversion via HPLC. HPLC sample preparation ~10 uL of reaction mixture was diluted to 1 mL with 1:1 acetonitrile/10 mM ammonium acetate pH 4.5. After 20 h at room temperature another portion of NCA (41 mg, 1.5 equiv.) was added and the reaction allowed to proceed at room temperature with periodic monitoring by HPLC. At the 20 hour mark, the percent conversion of maytansinol to the N-methylalanine ester Aa was about 71% and the percent diastereomeric excess was 95%. After 40 hours, HPLC analysis showed an 84% conversion of the maytansinol to the ester Aa and the percent diastereomeric excess was 93%.

DM1-SMe may be prepared by coupling 3-(S)-α-N-methylaminopropionate (Aa) with 3-(2-methyldisulfanyl)propanoic acid, HO$_2$CCH$_2$CH$_2$SSMe (2):

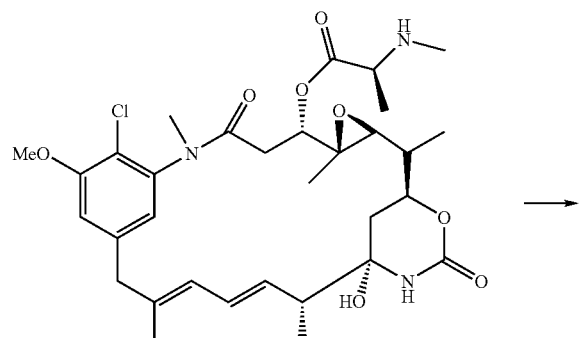

Aa (N-methylalanine ester)

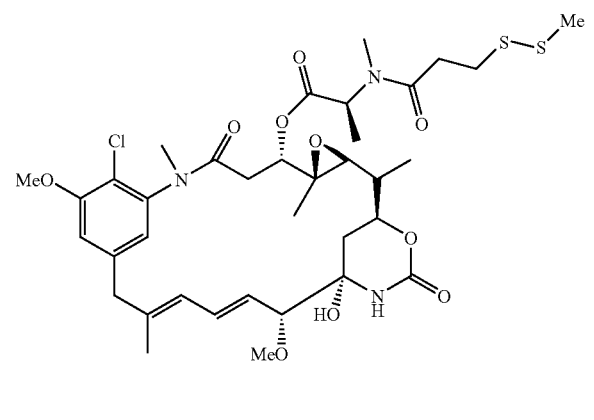

DM1-SMe

A variety of ways for carrying out the above reaction are within the knowledge of those skilled in the art. For example, an active ester form of the acid 2, such as the N-hydroxysuccinimide (—OSu) or pentafluorophenyl (—Pf) ester, may be used in the coupling reaction. Alternatively, DM1 may be prepared by coupling the free acid 2 with a suitable coupling reagent. Examples of coupling reagents include uronium-type coupling agents such as, but not limited to, O-[cyano (ethoxycarbonyl)methylenamino]-N,N,N',N'-tetramethyluronium tetrafluoroborate (TOTU), 2-(7-Aza-1H-benzotriazole-1-yl)-1,1,3,3-tetramethyluronium hexafluorophosphate (HATU), HBTU, or TBTU (2-(1H-Benzotriazole-1yl)-1,1,3,3-tetramethyluronium hexafluorophosphate and tetrafluoroborate respectively); a carbodiimide type reagent such as, but not limited to, DCC (dicyclohexylcarbodiimide), DIC (diisopropylcarbodiimide), or EDC (1-Ethyl-3-(3-dimethylaminopropyl)-carbodiimide); active esters; or phosphonium type coupling reagents such as, for example, Bop (benzotriazol-1-yloxy-tri(dimethylamino)-phosphonium hexafluorophosphate) or PyBOP (benzotriazol-1-yloxy-tri(pyrrolidino)-phosphonium hexafluorophosphate). Other useful coupling reagents include IIDQ (2-isobutoxy-1-isobutoxycarbonyl-1,2-dihydroquinoline), EEDQ (2-ethoxy-1-ethoxycarbonyl-1,2-dihydroquinoline) and isobutylchloroformate. Peptide coupling is described, for example, in Humphrey and Chamberlin, Chem. Rev. 1997, 97, 2243-2266, incorporated herein by reference in its entirety.

In one example, the following procedure was employed to convert 3-(S)-α-N-methylaminopropionate (Aa) to DM1-SMe. Diisopropylethylamine (51 microliters, 0.29 mmol) was added to a solution of crude A (95 mg, 0.146 mmol, obtained according to the example described above) in methylene chloride (1.8 mL). After the solution was stirred for 2-3 minutes, 3-methyldisulfanyl-propionic acid 2,5-dioxo-pyrrolidin-1-yl ester (55 mg, 0.22 mmol) was added. The stirred reaction mixture was then heated to 30-35° C. for 16 hours. HPLC analysis indicated that the reaction mixture contained about 45-50% DM1-SMe and 30-35% maytansinol (from the previous step). The ratio of L isomer to D isomer remained unchanged at about 98:2.

The conversion of DM1-SMe to DM1 may be accomplished by cleavage of the disulfide bond in a known manner. For example, dithiothreitol (DTT) is a reagent of choice for such conversions. Tetrahedron Lett. 1993, 34, 8169.

Maytansinol 3-(S)-α-N-methylaminopropionate (Aa) is a useful intermediate for making other maytansinoids such as DM4:

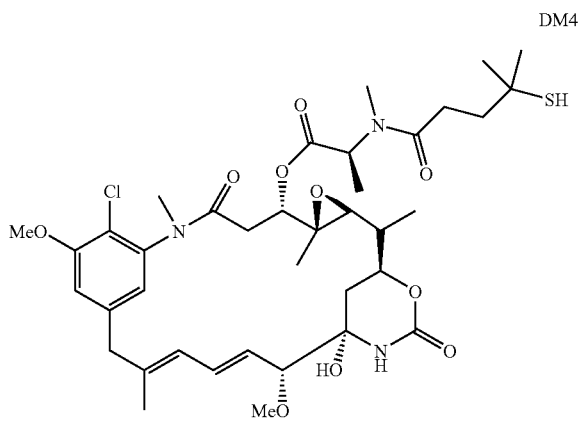

DM4

-continued

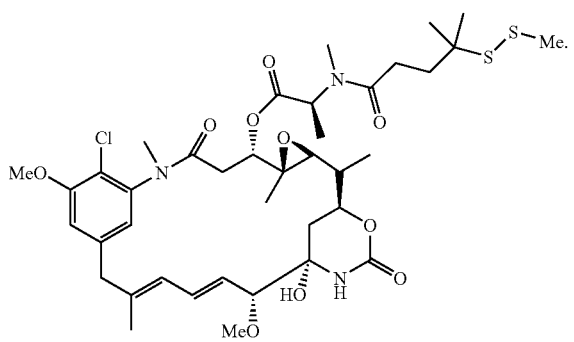

DM4-SMe

In a manner analogous to the preparation described above for DM1-SMe, DM4-SMe may be obtained from intermediate Aa by replacing 3-(2-methyldisulfanyl)propanoic acid with 4-methyl-4-(2-methyldisulfanyl)pentanoic acid, $HO_2CCH_2CH_2C(CH_3)_2SSMe$, or an activated form thereof. DM4-SMe may then be converted to DM4 by reduction of the disulfide bond as described above.

For use as anti-tumor agents, DM1 and DM4 may be conjugated to an antibody by the formation of a disulfide bond between the sulfur atom of the drug and the sulfur atom of an antibody linker group. Compared to DM1, the sulfur of DM4 is more sterically hindered as a result of the methyl groups adjacent to the sulfur. This steric hindrance is designed to make the antibody-drug conjugate more chemically stable. In designing various maytansinoids one can adjust the stability of the conjugate by introducing various other substituents next to the sulfur. In this manner, one may optimize the potency and tolerability of the drug-antibody conjugate as needed for the particular anti-tumor antibody. An advantage of the present method is that intermediate A may be used for the preparation of a variety of DM type side chains having various chain lengths and substituents on the mercapto-alkanoyl moiety attached to the N-methyl-alanyl portion of the side chain.

The present method is also useful for making compounds that are analogs of maytansines with various chiral amino acid side chains. A number of maytansine and maytansinol syntheses have been reported. The reported syntheses enable the preparation of various analogs which may undergo the coupling reaction with a 4-alkyl-1,3-oxazolidine-2,5-dione or 3,4-dialkyl-1,3-oxazolidine-2,5-dione, such as 1, and subsequent elaboration of the side chain suitable for conjugation to an antibody. Furthermore, maytansinol is one member of a class of ansa macrolides, a number of which have been isolated from microorganisms and shown to have cytotoxic activity (Merck Index, 13$^{th}$ Edition, 2001). One such analog is identical to maytansinol except that hydrogen is found where there is a chloro substituent on the phenyl moiety of the macrolide.

Typically, the substituted 1,3-oxazolidine-2,5-dione used is homochiral or enantiomerically-enriched, wherein the predominant isomer is the S-isomer. Naturally occurring amino acids provide a variety of 1,3-oxazolidine-2,5-diones where the carbon bearing the $R^1$ group has this desired configuration. Preferred $R^1$ groups include, for example, small substituted or unsubstituted alkyl groups such as methyl, isobutyl, or benzyl. $R^2$ may be hydrogen or a small alkyl group. It is also preferred that the non-nucleophilic base in step (a) is an organic base, more preferably one of the hindered organic bases described above.

As mentioned above, the present invention is amenable to the preparation of a wide range of maytansines having a secondary amino acid side chain for conjugation to an antibody. Accordingly, another embodiment of the invention relates to a method of making a compound of formula II:

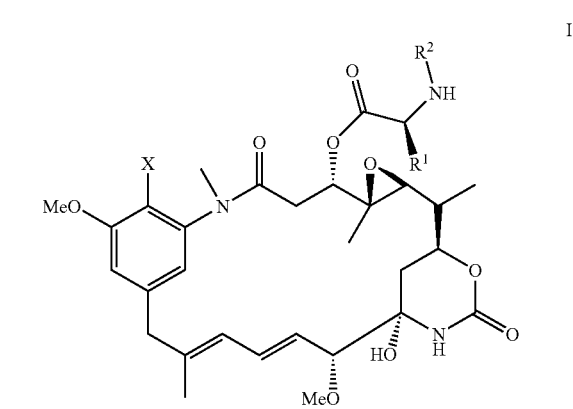

II wherein:

X is Cl or H;

$R^1$ is an amino acid side chain;

$R^2$ is hydrogen or $C_{1-6}$ alkyl;

L is a $C_{2-6}$ alkylene chain having 0-2 substituents independently selected from the group consisting of halo, $C_{1-6}$ alkyl, $C_{1-6}$ alkoxy, $C_{1-6}$ haloalkyl, and $C_{1-6}$ haloalkoxy;

$R^3$ is hydrogen or S—$R^4$; and $R^4$ is $C_{1-6}$ alkyl, aryl, or aralkyl.

The method comprises the steps of:

(a) obtaining a compound of formula I:

I

-continued

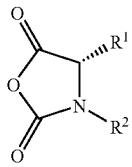

by a coupling reaction of 2 with maytansinol or its analogue where X=H;

(b) coupling the compound of formula I obtained from step (a) with $R^5O_2C$—L—S—S—$R^4$, where $R^5$ is hydrogen or an activating group to provide the compound of formula II where $R^3$ is S—$R^4$; and (c) optionally treating the compound of formula II obtained in step (b) with a reducing agent to provide a compound of formula II where $R^3$ is hydrogen.

A preferred starting material is maytansinol (X=Cl). Preferably L is a $C_{2-3}$ alkylene chain having 0-2 substituents independently selected from $C_{1-6}$ alkyl and more preferably the alkylene chain is substituted by 0-2 methyl groups. Most preferably $R^5O_2C$—L-S—S—$R^4$ is selected from

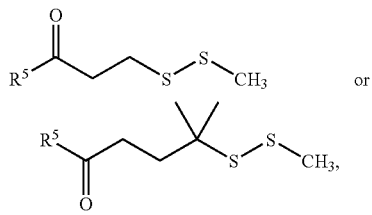

which provide DM1-SMe and DM4-SMe, respectively. To provide a side chain that is suitable for antibody conjugation, the compound of formula II obtained in step (b) above is treated with a reducing agent, such as dithiothreitol, to provide a compound of formula II where R is hydrogen.

The maytansinoids prepared by the present method may be conjugated to a variety of antibodies. In addition to the aforementioned MLN2704, which is a conjugated PSMA antibody, examples of other DM-conjugated antibodies include cantuzmab mertansine/huC242-DM1 which targets the CanAg antigen for the treatment of colorectal, gastric, pancreatic and certain non-small cell lung cancers, huN901-DM1 which targets the CD56 antigen for the treatment of non-small cell lung cancers, neuroendocrine tumors and certain hematological cancers, and trastuzumab-DM1 which targets the Her2 antigen for the treatment of Her2 tumors.

While the foregoing invention has been described in some detail for purposes of clarity and understanding, these particular embodiments are to be considered as illustrative and not restrictive. It will be appreciated by one skilled in the art from a reading of this disclosure that various changes in form and detail can be made without departing from the true scope of the invention, which is to be defined by the appended claims rather than by the specific embodiments.

What is claimed is:

1. A method of making a compound of formula A:

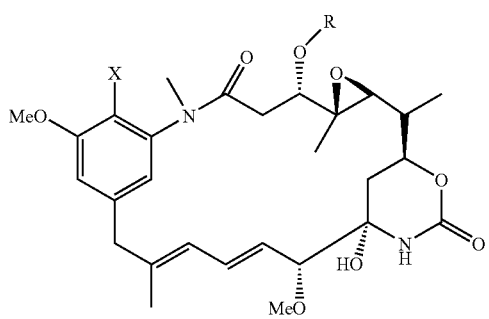

where:
X is Cl or H, and
R is

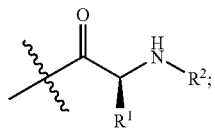

$R^1$ is a naturally-occurring amino acid side chain;
$R^2$ is hydrogen or a $C_{1-6}$ alkyl group;
said method comprising:
(a) providing a mixture comprising
  (i) a starting material which has a formula identical to formula A except that R is hydrogen,
  (ii) a compound of formula 2:

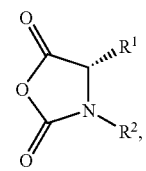

(iii) a Lewis acid,
  (iv) a non-nucleophilic base and
  (v) an organic solvent;
(b) allowing the mixture of step (a) to react until some of the starting material is converted to the compound of formula A;
(c) removing crude compound of formula A from the mixture of step (b); and
(d) optionally purifying the compound of formula A obtained in step (c).

2. The method of claim 1 wherein the starting material is maytansinol.

3. The method of claim 2 where $R^1$ is a $C_{1-6}$ alkyl and $R^2$ is a $C_{1-6}$ alkyl.

4. The method of claim 3 wherein 2 is predominantly (S)-isomer.

5. The method of claim 4 wherein 2 is 3,4-dimethyl-oxazolidine-2,5-dione.

6. A method of making a compound of formula II:

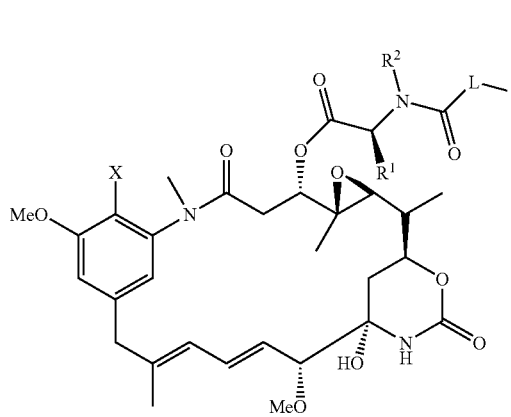

wherein:
X is Cl or H;
$R^1$ is a naturally-occurring amino acid side chain;
$R^2$ is hydrogen, $C_{1-6}$ alkyl, aryl or aralkyl;
L is a $C_{2-6}$ alkylene chain having 0-2 substituents independently selected from the group consisting of halo, $C_{1-6}$ alkyl, $C_{1-6}$ alkoxy, $C_{1-6}$ haloalkyl, and $C_{1-6}$ haloalkoxy;
$R^3$ is hydrogen or S—$R^4$; and
$R^4$ is $C_{1-6}$ alkyl, aryl, or aralkyl;
the method comprising:
(a) obtaining a compound of formula I:

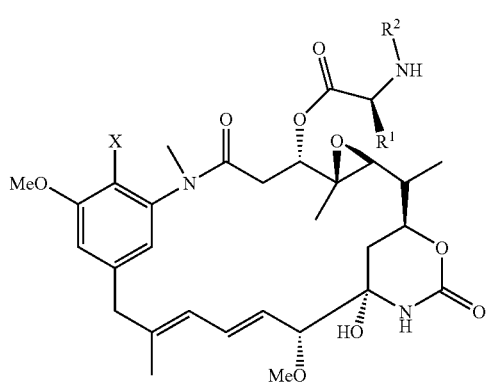

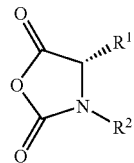

by a coupling reaction of 2 with maytansinol or its analogue where X=H, wherein the coupling reaction is performed in the presence of a Lewis acid, a non-nucleophilic base and an organic solvent;

(b) coupling the compound of formula I obtained from step (a) with $R^5O_2C$—L—S—S—$R^4$, where $R^5$ is hydrogen or an activating group to provide the compound of formula II where $R^3$ is S—$R^4$; and (c) optionally treating the compound of formula II obtained in step (b) with a reducing agent to provide a compound of formula II where $R^3$ is hydrogen.

7. The method of claim 6 where $R^2$ is hydrogen or $C_{1-6}$ alkyl and L is a $C_{2-3}$ alkylene chain having 0-2 substituents independently selected from $C_{1-6}$ alkyl.

8. The method of claim 7 where L is an alkylene chain substituted by 0-2 methyl groups.

9. The method of claim 8 where $R^5O_2C$—L—S—S—$C_{1-6}$ alkyl is:

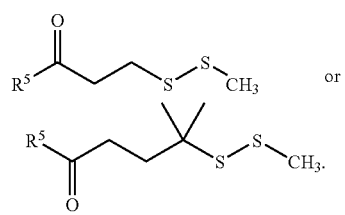

10. The method of claim 9 wherein the compound of formula II obtained in step (b) is treated with a reducing agent to provide a compound of formula II where $R^3$ is hydrogen.

* * * * *